United States Patent [19]

Smith et al.

[11] Patent Number: 4,590,196
[45] Date of Patent: May 20, 1986

[54] ANALGESIC 1,2-BENZISOTHIAZOL-3-YLPIPERAZINE DERIVATIVES

[75] Inventors: David W. Smith, Evansville; Joseph P. Yevich, Newburgh, both of Ind.

[73] Assignee: Bristol-Myers Company, New York, N.Y.

[21] Appl. No.: 643,614

[22] Filed: Aug. 23, 1984

[51] Int. Cl.$^4$ .................. C07D 417/04; A61K 31/495
[52] U.S. Cl. ...................................... 514/253; 544/368
[58] Field of Search .................. 544/368; 424/250; 514/253

[56] References Cited

U.S. PATENT DOCUMENTS

| | | | |
|---|---|---|---|
| 4,104,388 | 8/1978 | Wade et al. | 544/368 |
| 4,112,105 | 9/1978 | Carlson et al. | 544/368 |
| 4,355,037 | 10/1982 | Strupczewski et al. | 424/267 |
| 4,396,770 | 8/1983 | Davis et al. | 424/267 |
| 4,411,901 | 10/1983 | Temple et al. | 544/368 |
| 4,452,799 | 6/1984 | Temple et al. | 544/368 |

OTHER PUBLICATIONS

Chem. Abstracts, 71, (1969), 389541.
Chem. Abstracts, 61, (1964), 12008.

*Primary Examiner*—George F. Lesmes
*Assistant Examiner*—S. A. Gibson
*Attorney, Agent, or Firm*—Richard P. Ryan; Robert H. Uloth

[57] ABSTRACT

A series of non-opiate analgesics of Formula I

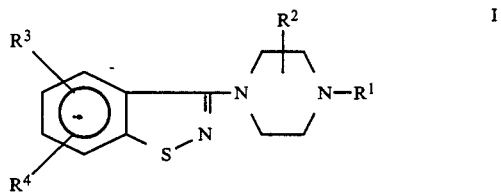

wherein $R^1$ is hydrogen, alkyl, aralkyl, or aryloxyalkyl; $R^2$ is alkyl or hydrogen; and $R^3$ and $R^4$ are independently selected from hydrogen, alkyl, acyloxy, alkoxy, alkylthio, halogen, hydroxyl, or trifluoromethyl; or a pharmaceutically acceptable acid addition salt.

26 Claims, No Drawings

ANALGESIC 1,2-BENZISOTHIAZOL-3-YLPIPERAZINE DERIVATIVES

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is 1,2-benzisothiazol-3-yl, unsubstituted or substituted in its benzoring; and the other substituent is, inter alia, alkyl, cycloalkyl, aralkyl, and phenoxyalkyl.

Related art may be viewed in light of the following general structural Formula I

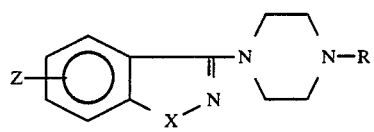

in which R and Z are substituents and X is a hetero ring atom or grouping. The most closely related art appears to be that contained in two issued patents assigned to Bristol-Myers and Company.

In U.S. Pat. No. 4,411,901, issued on Oct. 25, 1983, to Temple and Yevich, a series of neuroleptic agents of structure 2 is disclosed

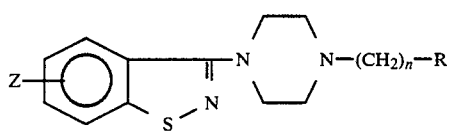

wherein Z is hydrogen or halogen and R represents the radical:

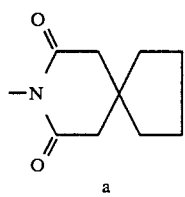
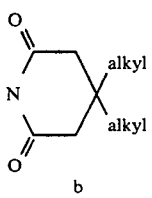
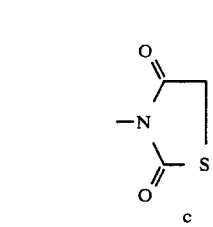
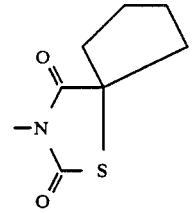
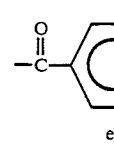
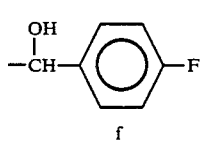

and n is 3 or 4. As can be seen, the R- substituents a-d are heterocyclic rings, whereas incorporation of e and f into structure 2 produces antipsychotic butyrophenone derivatives. A synthetic intermediate compound (3) was also disclosed

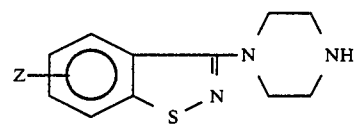

and was claimed in the related divisional U.S. Pat. No. 4,452,799, issued June 5, 1984.

A series of compounds disclosed as anti-inflammatory agents by Wade and Kissick in U.S. Pat. No. 4,104,388, issued Aug. 1, 1978, have structural formula 4.

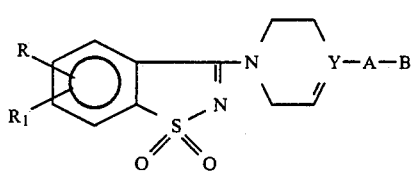

wherein Y can be C or N; A is a single bond or a 1–4 carbon alkylene chain; and B is hydrogen, hydroxyl, or optimally substituted phenyl. These compounds are easily distinguished as they are 1,1-dioxide ring derivatives of benzisothiazole.

The following references, while related, are less relevant to the new compounds disclosed in this application.

Strupczewski, et al, in U.S. Pat. No. 4,355,037, issued Oct. 19, 1982, disclosed a series of benzisoxazolyl piperidine derivatives (5) described as analgetic agents.

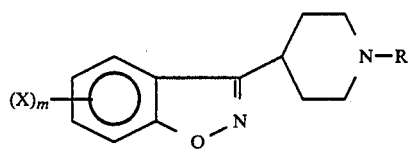

In structure (5), R can be hydrogen, alkyl, alkenyl, cycloalkylalkyl, phenalkyl, hydroxy, aminoalkyl, cyano, cyanoalkyl, alkanolyl, or a carboxylic acid ester moiety.

Even further removed is a series of benzisoxazole-piperidine compounds shown as structure 6

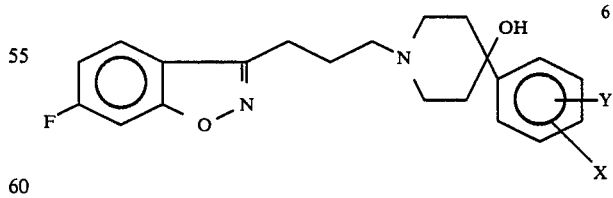

which were disclosed as anti-psychotics and analgesics by Davis and Klein in U.S. Pat. No. 4,396,770, issued Aug. 2, 1983.

As can be seen, there is nothing in the foregoing references concerning related art which would suggest or make obvious the compounds of the present invention.

SUMMARY OF THE INVENTION

A series of 1-(1,2-benzisothiazol-3-yl)piperazine-4-yl derivatives of Formula I have been synthesized:

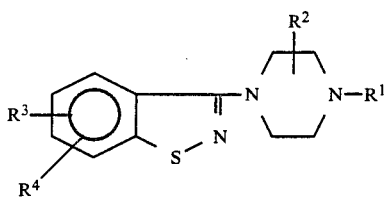

I wherein $R^1$ is hydrogen, lower ($C_{1-6}$) alkyl, either straight chained or branched, lower alkenyl, lower cycloalkyl, lower cycloalkyl-lower alkylene, phenyl-lower alkylene, phenoxy-lower alkylene, phenyl-lower cycloalkyl, or benzodioxan-2-yl-lower alkylene; $R^2$ is lower alkyl or hydrogen; and $R^3$ and $R^4$ are independently chosen from hydrogen, lower alkyl, lower acyloxy, lower alkoxy, lower alkylthio, halogen, or hydroxyl or trifluoromethyl; or a pharmaceutically acceptable acid addition salt thereof. Pharmacological testing has demonstrated that these compounds possess analgesic activity. Additionally, the lack of affinity shown for the opioid receptor and intrinsic affinity for both the serotonergic and adrenergic receptor types in vitro suggests that these compounds may be novel non-opiate analgesic agents.

DETAILED DESCRIPTION OF THE INVENTION

In its broadest aspect, the prsent invention is concerned with 1,2-benzisothiazol-3-yl-piperazine derivatives having analgesic properties characterized by compound of Formula I

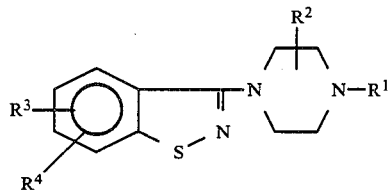

I wherein $R^1$ is hydrogen, lower ($C_{1-6}$) alkyl, either straight chained or branched, lower alkenyl, lower cycloalkyl, lower cycloalkyl-lower alkylene, phenyl-lower alkylene, phenoxy-lower alkylene, phenyl-lower cycloalkyl, or benzodioxan-2-yl-lower alkylene; $R^2$ is lower alkyl or hydrogen; and $R^3$ and $R^4$ are independently chosen from hydrogen, lower alkyl, lower acyloxy, lower alkoxy, lower alkylthio, halogen, hydroxyl or trifluoromethyl; or a pharmaceutically acceptable acid addition salt thereof. $R^1$ is other than hydrogen when $R^2$, $R^3$ and $R^4$ are all hydrogen. It is to be understood that, as used herein, halogen denotes fluorine, chlorine, bromine, or iodine. Preferred compounds of structure I have $R^1$ groups with four or more carbon atoms and most preferred compounds are those in which $R^1$ is cycloalkyl.

It is also to be understood that the present invention is to be considered to include any and all steroisomers which can arise as a consequence of structural asymmetry which would be evident to one skilled in the chemical arts. Separation of the individual stereo-isomers, should they exist, would be accomplished by application of various methods which are well known to chemical practitioners.

For medicinal use, the pharmaceutically acceptable acid addition salts, those salts in which the anion does not contribute significantly to toxicity of pharmacological activity of the organic cation, may be preferred. The acid addition salts are obtained either by reaction of an organic base of structure I with an organic or inorganic acid, preferably by contact and solution or by any of the standard methods detailed in the literature available to any practitioner skilled in the art. Examples of useful organic acids are carboxylic acids such as maleic acid, acetic acid, tartaric acid, propionic acid, fumaric acid, isethionic, succinic acid, pamoic acid, cyclamic acid, pivalic acid, and the like; useful inorganic acids are hydrohalide acids such as HCl, HBr, HI; sulfuric acid; phosphoric acid; and the like.

The compounds of the instant invention can be conveniently prepared by use of the process which is shown in Scheme 1.

SCHEME 1

Process for Preparation of Formula I Compounds

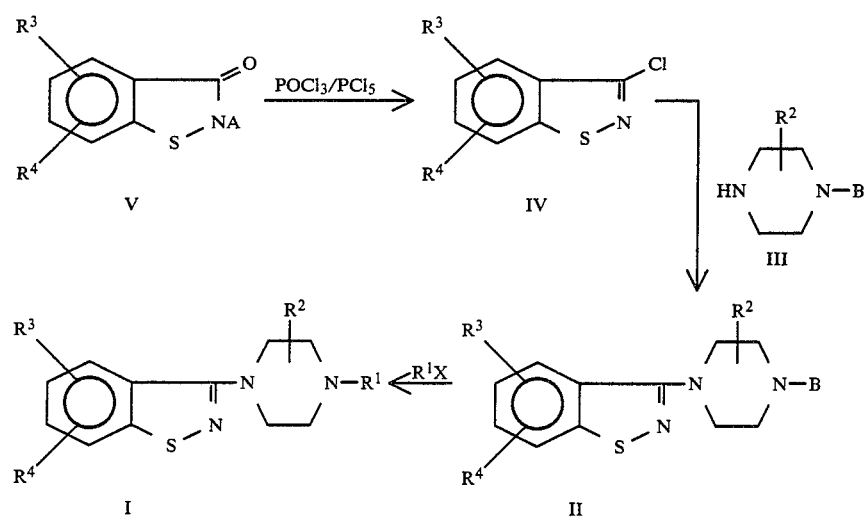

In this scheme, $R^1$–$R^4$ have the same meanings as previously assigned to them in Formula I. The symbol A can be hydrogen or t-butyl and B can be hydrogen or a t-butyloxy carbonyl moiety. The choice of moiety for A is not important in the process as it is lost in the conversion of V to IV. When B is the t-butyloxy carbonyl moiety (a blocking group), it is cleaved to give the appropriate IV or II compound wherein B is H prior to further reaction, e.g. reaction with $R^1X$ to obtain product I.

Essentially, the synthetic process depicted in Scheme 1 comprises:

(1) a 1,2,-benzisothiazol-3-(2H)-one, V, is treated with a strong chlorinating agent, e.g. $POCl_3$ or $PCl_5$, to yield a 3-chloro-1,2-benzisothiazole, IV. The conversion of V to IV by the use of various halogenating agents has been adequately described in the chemical literature, cf: N. Davis, "Benzisothiazoles" in *Advances in Heterocyclic Chemistry*, Vol. 14, Edited by A. R. Katritzky and A. J. Boulton, and various references therein.

(2) the 3-chloro-1,2-benzisothiazole, IV, is reacted with an appropriate piperazine intermediate, III, to give a 3-(1-piperazinyl)-1,2-benzisothiazole, II. The reaction conditions employed for this step are those which are commonly used for this type of nucleophilic displacement reaction. If III is a liquid, these reactions are often run neat. For certain intermediate compounds of structure IV, yields may be optimized and isolation of intermediate II made easier by using an N-t-butyloxy carbonyl piperazine intermediate of III (wherein B is t-butyloxy carbonyl). In cases such as these, the blocking N-t-butyloxy carbonyl group is removed from II by acid hydrolysis prior to its use in the following step. The removal of this blocking t-butyloxy carbonyl group occurs readily upon treatment with ethanolic HCl.

(3) The 3-(1-piperazinyl)-1,2-benzisothiazole, II, is alkylated with $R^1X$ to afford the desired product of formula I. In this reaction step the intermediate II is dissolved in an inert solvent, preferably acetonitrile, and treated with one equivalent of a hindered base, preferably N,N-diisopropylethylamine, followed by treatment with $R^1X$, wherein X is a typical leaving group such as halide, tosylate, mesylate, and the like. This reaction is usually complete following heating at reflux for several hours.

It should be stated that other synthetic methods in addition to simple alkylation which, in effect, accomplish the same structural conversion of II to I, may be employed. An example of such a method would be reductive amination of compounds of structure II (B=H) with a carbonyl compound to yield a product of structure I. An example of this alternative synthetic method is shown below.

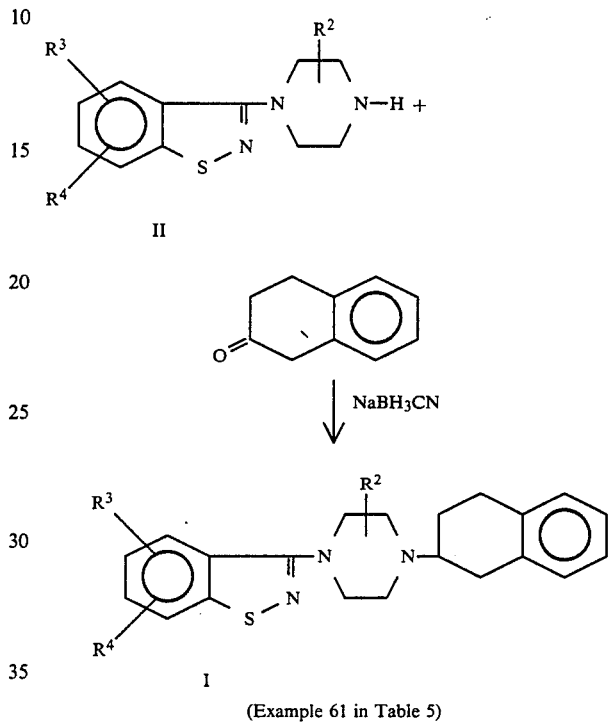

(Example 61 in Table 5)

Various synthetic methods may be employed for the preparation of certain formula V intermediary 1,2-benzisothiazolones when these are not readily available. Several of these methods are outlined below in Scheme 2.

SCHEME 2

Methods of Preparation for Formula V Intermediates

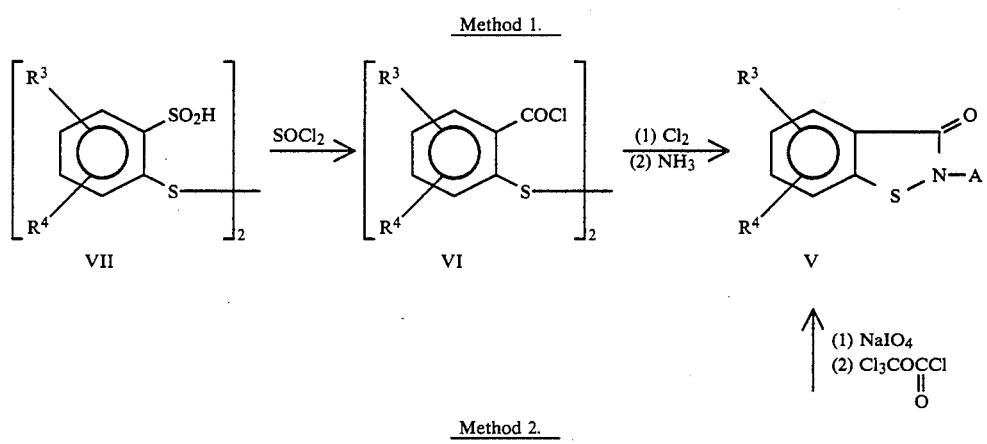

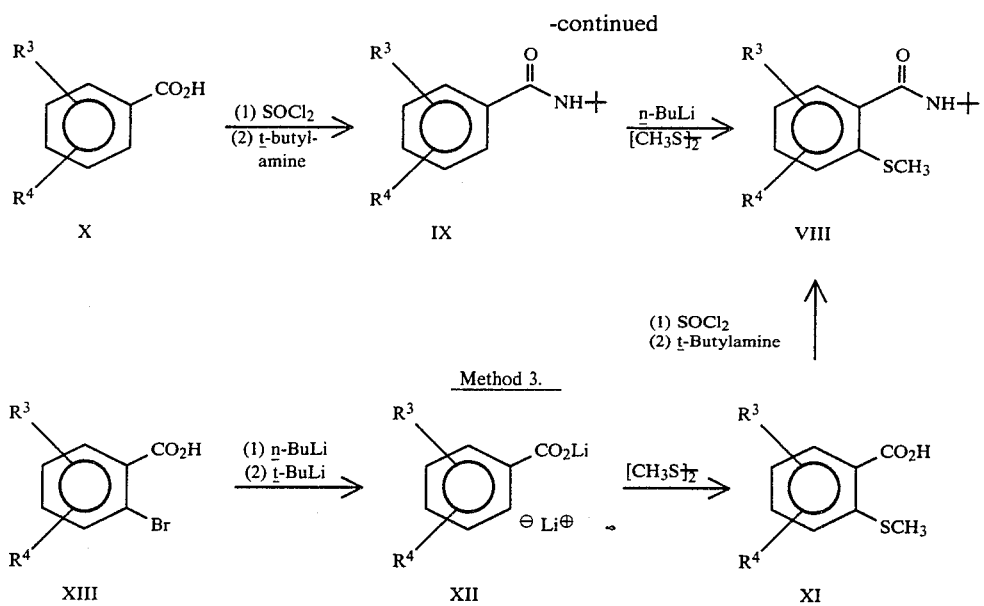

Method 3.

In most instances, any of the methods shown in Scheme 2 may be utilized for preparation of the desired intermediate compound V. Preference of method is based on availability of starting compounds and ease of isolation of the various intermediate compounds particular to each method. Method 1 requires suitably substituted dithiosalicylic acids, VII, which are then converted to the corresponding acid chlorides, VI, in high yield with thionyl chloride. Sequential reaction of intermediate VI with chlorine followed by ammonia affords the desired intermediate product, V.

Method 2, which is the most general and most widely applicable method, begins with an appropriately substituted benzoic acid, X, which is converted to a t-butyl benzamide, IX, by treatment with thionyl chloride followed by t-butylamine. This benzamide, IX, undergoes ortho-metallation with n-butyllithium followed by sulfination with methyl disulfide to provide compound VIII. Oxidation of the S-methyl intermediate, VIII, by meta-chloroperbenzoic acid or sodium periodate provides the corresponding sulfoxide which is converted to the desired intermediate product V by treatment with trichloromethyl chloroformate.

Method 3 is a variation of Method 2 which is employed for preparation of those V compounds when the benzamide intermediate, IX, e.g. 5-methoxybenzoic acid, does not undergo the desired regiochemical ortho-directed metallation. In this instance, an ortho-bromobenzoic acid, XIII, is treated with t-butyllithium and undergoes metal-halogen exchange to give the ortho-anion, XII, which then reacts with dimethyl disulfide to yield intermediate XI. This ortho-methylthiobenzoic acid is then converted at this point into intermediate compound, VIII, and then on to the final intermediate, V, as shown in Scheme 2.

Various modifications and adaptations of methods 1-3 would be obvious to one skilled in the chemical arts. Examples of Methods 1-3, including synthesis of pertinent intermediates, will be exemplified later in the specification.

The compounds of the instant invention are useful pharmacological agents which display analgesic activity in mammals. The following in vivo tests (Table 1) were used to evaluate and classify the instant series of compounds.

TABLE 1

In Vivo Tests Used To Evaluate Formula I Compounds

1. Conditioned Avoidance Response (CAR)—Measure of a drug's tranquilizing activity as determined by its attenuation of avoidance response to electrical shock in trained fasted rats.
2. Inhibition of Norepinephrine Lethality—Drug inhibition of the lethality of the noradrenergic agent norepinephrine indicates adrenergic blockade.
3. Vocalization Threshhold—Measure of a drug's analgesic activity as determined by its ability to prevent electrical shock-induced vocalization in rats.
4. Phenylquinone Writhing—Measure of a drug's analgesic activity as determined by its ability to prevent the writhing syndrome induced by phenylquinone in mice.

Additionally, the following in vitro radioreceptor binding assays were utilized to determine intrinsic affinity of compounds of the instant series for specific binding sites:

1. Dopamine binding in striatal tissue versus [$^3$H]spiperone
2. $\alpha_1$-adrenergic binding versus [$^3$H]WB-4101
3. Serotonin type 2 binding in cortical tissue versus [$^3$H]spiperone.

According to the pharmacological profile established by the aforementioned tests, the instant compounds of Formula I possess analgesic action of sufficient potency to render this series of compounds promising candidates as non-opiate analgesics. Results of the in vitro binding studies, listed above, indicate that adrenergic and serotonergic mechanisms appear to be involved in mediation of analgesia for this series.

Concerning the in vivo test data, phenylquinone writhing and vocalization threshold measurements were the main screening tests utilized as predictive of analgesic activity. Most of the compounds of the instant series had activities below 10 mg per kg in the vocalization threshhold test and less than 100 mg per kg in the phenylquinone writhing test. The conditioned avoidance response and inhibition of norepinephrine lethality test are more predictive of antipsychotic and sedative actions respectively. Results from these tests indicate that the instant compounds have low levels of activity in these tests which may indicate a decreased liability for side effects.

In summary, the instant compounds have pharmacologic properties suited to their use as non-opiate analgesics. Thus, another aspect of the instant invention concerns a process for inducing analgesia in a mammal in need of such treatment which comprises systemic administration to such mammal of an effective analgesic dose of a Formula I compound or a pharmaceutically acceptable acid addition salt thereof. The administration and dosage regimens of compounds of Formula I would be expected to be done in the same manner as for the reference compound nefopam (see for example, Heel, et al., Drugs, 19, pages 249–267 (1980)). Although the dosage and dosage regimen must in each case be carefully adjusted, utilizing sound professional judgment and considering the age, weight and condition of the recipient, the route of administration and the nature and gravity of the illness, generally the daily dose will be from about 30 to 600 mg administered from 1 to 3 times per day. It is to be expected that dosage amounts will be in the lower part of this range when given parenterally and in the upper end of the range when given orally. In some instances, a sufficient therapeutic effect can be obtained at lower doses while in others, larger doses will be required.

The term "systemic administration" as used herein refers to oral, rectal, and parenteral (i.e., intramuscular, intravenous, and subcutaneous) routes. Generally, it will be found that when a compound of the present invention is administered orally, which is the preferred route, a larger quantity of the active agent is required to produce the same effect as a smaller quantity given parenterally. In accordance with good clinical practice, it is preferred to administer the instant compounds at a concentration level that will produce effective analgesic effects without causing any harmful or untoward side effects. Since the instant compounds are non-opiate analgesics, not only are the typical opiate side effects circumvented, but the potential exists for concomitant analgesic use of these agents with opiate analgesics.

Therapeutically, the instant compounds are generally given as pharmaceutical compositions comprised of an effective analgesic amount of a compound of Formula I or a pharmaceutically acceptable acid addition salt thereof in a pharmaceutically acceptable carrier. Pharmaceutical compositions for effecting such treatment will contain a major or minor amount, from 95 to 0.5% of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e. physically discrete units containing a predetermined amount of the drug corresponding to a fraction or multiple of the dose which is calculated to produce the desired therapeutic response. The dosage units may contain one or more single doses, or alternatively, one-half or one-third, or less, of a single dose. A single dose preferably contains an amount sufficient to produce the desired therapeutic effect upon administration at one application of one or more dosage units according to the predetermined dosage regimen, usually a whole, half, or third of the daily dosage administered from one to three times a day. Other therapeutic agents may also be present. Pharmaceutical compositions which provide from about 30 to 600 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinylpyrrolidone). Fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerin, propyleneglycol, and polyethyleneglycols or mixtures thereof. The polyethyleneglycols consist of a mixture of non-volatile, usually liquid, polyethyleneglycols which are soluble in both water and organic liquids and which have molecular weights of from about 200 to 1500.

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C. when not specified.

The nuclear magnetic resonance (NMR) spectral characteristics refer to chemical shifts ($\delta$) expressed as parts per million (ppm) versus tetramethylsilane (TMS) as reference standard. The relative area reported for the various shifts in the proton (NMR) spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), or quartet (q). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

SYNTHESIS OF INTERMEDIATES

A. Formula V Compounds

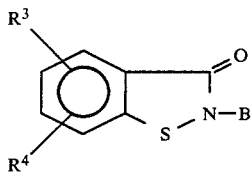

EXAMPLE 1

1,2-Benzisothiazol-3(2H)-one (Method 1)

A slurry of 2,2'-dithiosalicylic acid (2017 g, 6.584 moles), thionyl chloride (1645 g, 13.826 moles), toluene (10 liter) and N,N-dimethylformamide (40 mL) was heated at about 75° for 18 hours. At this point all solid had dissolved and the resulting dark solution was cooled to 8°. The reaction product crystallized and was isolated by filtration and washed on the filter with about 1 liter of cold Skelly F. Drying yielded 1619 g (71%) of 2,2'-dithio-bis-benzoyl chloride, m.p. 154°–156° (Lit. m.p. 155°–156°; cf: I. R. Douglass and B. S. Farrah, J. Org. Chem., 26, 351–354 (1961)).

Chlorine (239 g, 3137 moles) was bubbled into a stirred suspension of 2,2'-dithio-bis-benzoyl chloride (1157 g, 3.37 moles) and methylene chloride (8.46 liter). The resulting solution was added to conc. $NH_4OH$ (2.89 liter) with vigorous stirring. The mixture was stirred for one hour after the addition was complete. Filtration yielded a damp solid which was suspended in about 7 liters of water and acidified by adding conc. aqueous HCl with vigorous stirring. The solid was isolated by filtration and washed on the filter with about 3 liters of water. Drying in vacuo at 30° gave 902 g (88.5%) of product, m.p. 155.5°–157°.

EXAMPLE 2

General Preparation (Method 2)

The appropriate benzoic acid is suspended in chloroform (1 mL $CHCl_3$ per 1 g acid) and two drops of DMF. A single portion of thionyl chloride (4 mole equiv.) is added at room temperature and the resulting mixture slowly warmed to reflux while being stirred. The mixture clears as the reaction progresses, with times of reflux typically ranging from 2 to 4 hours. The completed reaction is cooled to room temperature and concentrated in vacuo to the crude corresponding benzoic acid chloride compound in about 95% yield. A methylene chloride solution of the intermediate acid chloride (50 mL $CH_2Cl_2$ per 0.10 mole acid chloride) is added to a solution of triethylamine and t-butylamine in methylene chloride at 0°. The reaction is allowed to warm to room temperature and stand for approximately 18 hours. The mixture is then washed with 1.5N HCl, then with 0.5N NaOH solution, and finally with brine. Following washing, the reaction mixture is dried ($MgSO_4$), filtered and concentrated in vacuo to yield the crude amide in about 95% yield. The amide intermediate (IX) can be purified by recrystallization or Kugelrohr distillation to yield 71–76% of purified product.

The benzamide intermediate (IX; 0.025–0.40 mole) is dissolved in an anhydrous THF (500 mL) and chilled to −10° in an ice/acetone/salt bath while being stirred under a nitrogen atmosphere. To this cold, stirred reaction solution is added n-butyl lithium (2.5 mole equiv.) at a dropwise rate keeping the temperature at about −10°. Following completion of the addition, the reaction mixture is chilled to −78° (dry ice/acetone bath) for 15–30 minutes. Freshly distilled dimethyldisulfide (3 mole equiv.) is added dropwise at such a rate to keep the temperature less than −70°. The cold reaction solution is stirred one hour and then allowed to slowly warm where, at 0°, the reaction is quenched with 15% aqueous $NH_4Cl$ solution (2.75 mole equiv.). This mixture is concentrated in vacuo and partitioned between methylene chloride-water. The water layer is further extracted with methylene chloride and these organic portions combined, dried ($MgSO_4$), filtered, and concentrated in vacuo to the crude thiomethylbenzamide intermediate (VIII). The crude material which is obtained in about 90% yield may be used without further purification or may be purified by flash chromatography (hexane/ethyl acetate or hexane/methylene chloride).

The thiomethylbenzamide (VIII; 0.02–0.15 mole) is dissolved in methanol (200–500 mL) and added to aqueous 0.05N $NaIO_4$ (1.15 mole equiv.) under a nitrogen atmosphere while being stirred. The reaction is complete after 20 hours and the methanol is removed under reduced pressure. The resulting aqueous phase is extracted with methylene chloride and these organic extracts combined and dried ($MgSO_4$), filtered and concentrated in vacuo. The resulting solid is purified by flash chromatography (ethyl acetate) and then dissolved in dichloroethane (0.002 mole per 8 mL) and chilled to 0° with stirring under nitrogen. Trichloromethylchloroformate (1 mole equiv.) is added in a single portion while the solution is allowed to stir at room temperature for about 1 hour. A 10% sodium hydroxide solution (5 mole equiv.) is added to the reaction mixture with vigorous stirring which continues for up to 2 hours. The mixture is then extracted with methylene chloride, the extracts combined and dried ($MgSO_4$), filtered and concentrated in vacuo to crude V which may be purified by recrystallization.

EXAMPLE 3

N-t-Butyl-4-methoxy-1,2-benzisothiazolone

O-Anisic acid (0.38 mol) was suspended in 60 mL $CHCl_3$ and 3 drops DMF. A single volume of $SOCl_2$ (4 mole equiv.) was added at room temperature with vigorous reaction and the reaction was then refluxed. The reaction was monitored by IR for disappearance of the carboxylic acid carbonyl stretch at 1740 cm$^{-1}$ and appearance of the acyl carbonyl stretch at 1780 cm$^{-1}$. The reaction was judged complete after 24 hours. The solvent and excess reagent were removed via vacuum distillation (86 mmHg) affording the crude o-anisoyl chloride in >95% yield as an oil. The acid chloride was cooled, diluted with 50 mL $CHCl_3$ and added dropwise to a chilled (ice/$H_2O$) solution of TEA and t-butylamine (1.2 mole equiv. each) in 100 mL $CHCl_3$. Once addition was complete, the cooling bath was removed and the mixture stood at ambient temperature. The mixture was washed 3×1.5N HCl, 2×0.5N NaOH, and 1×brine. The chloroform was dried on $MgSO_4$, filtered, and concentrated in vacuo to approximately 93 g oil which was Kugelrohr distilled (110°/0.3 mmHg). The N-t-butyl-o-anisamide was obtained as a yellow oil in 95% yield.

The benzamide (0.05 mole) was dissolved in 500 mL anhydrous THF and chilled to −10° (MeOH/ice)

under N₂. n-BuLi (2.5 mole equiv.) was added dropwise at a rate to keep the temperature between −10° and 0°. The solution was stirred 30 min. at −10°, then chilled to −75° (CO₂/acetone) and distilled methyl disulfide (3.0 mole equiv.) was added at rate to keep the temperature between −75° and −70°. The cold reaction was slowly warmed and at −65° (2.75 mol eqv; 15% NH₄Cl aqueous solution) was added. The solution was concentrated in vacuo; the residue was partitioned between CH₂Cl₂ and water and extracted 3×CH₂Cl₂. The combined organic portions were dried on MgSO₄, filtered and concentrated in vacuo to a yellow solid. The crude material was judged acceptable by TLC and was used without further purification in 94% crude yield.

The thiomethyl benzamide (0.14 mole) was dissolved in 200 mL CH₂Cl₂ and stirred at −78° (CO₂/acetone) under N₂. A solution of m CPBA (1.2 mole equiv.) in 700 mL CH₂Cl₂ was added dropwise rapidly. The reaction was judged complete by TLC after 1 hour and was permitted to warm to ambient temperature. The mixture was concentrated in vacuo, then partitioned between CH₂Cl₂ and water. The mixture was extracted 3×H₂O and 3×10% aqueous K₂CO₃. The organic layer was dried on K₂CO₃, filtered and concentrated in vacuo to the crude material which was flash chromatographed (3% MeOH in CH₂Cl₂). The solid was recrystallized from 10% EtOAc in hexane and the crystalline sulfoxide was obtained in 74% yield.

The sulfoxide (0.08 mole) was dissolved in 160 mL of dichloroethane and warmed to 40° under N₂. Trichloromethyl chloroformate (1 mole equiv.) was added neat dropwise. Reaction was vigorous and warming was discontinued while the remaining chloroformate was added at room temperature. The mixture was then rewarmed to 70°. The reaction was judged complete by TLC after ½ hour. The reaction was cooled and poured into 170 mL of 10% NaOH (aqueous) and stirred vigorously ½ hour. The dichloroethane layer was removed and the aqueous phase was extracted 3×CH₂Cl₂. The combined organic phases were dried on MgSO₄, filtered and concentrated in vacuo. The crude material was flash chromatographed (40% EtOAc/60% hexane) affording the N-t-butyl-4-methoxy-1,2-benzisothiazolone in 80% yield.

EXAMPLE 4

5-Methoxy-N-t-butyl-1,2-benzisothiazol-3(2H)-one (Method 3)

2-Bromo-5-methoxybenzoic acid (0.005 mole) was dissolved in 50 mL of anhydrous tetrahydrofuran and chilled to −78° under nitrogen with stirring. n-Butyllithium (1.1 mole equiv.) was added dropwise at a rate to keep the temperature less than −70°. The yellow insoluble anion was then chilled to −115° (liquid nitrogen-ethyl ether bath) and t-butyllithium (1.4 mole equiv.) was added at a rate to keep the temperature less than −85°. When addition was complete, the insoluble dianion was warmed to −75°, whereupon it became soluble. Distilled methyl disulfide was added at a rate to keep the reaction temperature less than −70°. The bright yellow solution turned nearly colorless. The reaction was slowly warmed and quenched at −40° with 15% aqueous NH₄Cl (2.75 mole equiv.). The tetrahydrofuran was removed in vacuo, and the aqueous phase was washed three times with methylene chloride and then acidified with 6N HCl, then extracted three times with methylene chloride, dried (MgSO₄), filtered and concentrated in vacuo to a white solid. According to NMR spectra, the white solid consisted of a 65:35 mixture of 5-methoxy-1,2-thiomethylbenzoic acid and m-anisic acid, respectively.

The 5-methoxy-1,2-thiomethylbenzoic acid/m-anisic acid mixture (0.095 mole calculated as S-methyl material) was taken up in 80 mL chloroform and two drops DMF. Thionyl chloride (4 mole equiv.) was added at one time, and the solution heated to reflux. After refluxing for three hours, the reaction mixture was cooled to room temperature and concentrated in vacuo to the crude benzoic acid chloride mixture which was converted to the benzamide mixture by treatment with t-butylamine as in Example 2. At this point NMR indicated that the ratio of S-methyl anisamide to anisamide was approximately 9:2.

The N-t-butyl-5-methoxy-2-S-methyl benzamide/N-t-butyl anisamide mixture, used without further purification, (0.04 mole calculated as S-methyl material) was taken up in 450 mL of methanol and combined with 420 mL of 0.05M aqueous NaIO₄ under nitrogen. The reaction was complete in five hours and the methanol was removed under reduced pressure. The resulting aqueous phase was extracted with methylene chloride and these organic extracts were combined and dried (MgSO₄), filtered and concentrated in vacuo. The resulting solid was purified by flash chromatography (ethyl acetate) to give the solid sulfoxide intermediate in approximately 76% yield.

The N-t-butyl-5-methoxy-2-S-methyl sulfoxide benzamide was then treated with trichloromethylchloroformate using the procedure given in Example 2 to yield 5-methoxy-N-t-butyl-1,2-benzisothiazol-3(2H)-one, m.p. 92°–94°.

Other substituted benzisothiazolones, which can be prepared by the general synthesis of Method 2 are shown in Table 2.

TABLE 2
Substituted Benzisothiazolones

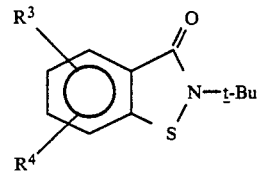

| Example No. | R³ | R⁴ | m.p. |
|---|---|---|---|
| 5 | 4-MeO | H | 141–143° |
| 6 | H | 6-MeO | 60–63° |
| 7 | H | 7-MeO | 118–120° |
| 8 | H | 6-Cl | 115–122° |
| 9 | 4-SCF₂ | H | |
| 10 | H | 6-SCF₃ | |
| 11 | H | 7-SCF₃ | |
| 12 | 4-OH | H | |
| 13 | 4-O₂CCH₃ | H | |
| 14 | H | 6-OH | |
| 15 | H | 6-O₂CCH₃ | |
| 16 | 4-CF₃ | H | |
| 17 | H | 6-CF₃ | |
| 18 | H | 7-CF₃ | |

B. Formula IV Compounds

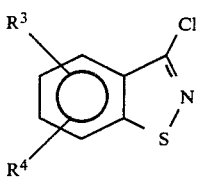

EXAMPLE 19

3-Chloro-1,2-benzisothiazole

A mixture of 1,2-benzisothiazole-3(2H)-one (Example 1, 818 g, 5.414 moles) and POCl₃ (1114 g, 7.26 moles) was heated to 120° over about two hours. HCl evolution began at about 70°. Heat was continued at 120° for another 1.5 hours. The hot solution was poured into 8 liter of H₂O at 25°. The temperature was not allowed to exceed 50°. After 30 minutes, the mixture was cooled to 25° (ice addition) and extracted with methylene chloride (4 liter). A dark oil was obtained by evaporation of the methylene chloride in vacuo. This oil was extracted with Skelly B (3×1 liter and 2×500 mL). The turbid extract was treated with Darco G-60 (30 g) and Celite A-545 (20 g) before filtering. The filtrate was evaporated in vacuo to give 743.9 g, 81%, of a yellow oil which readily crystallized. Distillation of the oil at reduced pressure gave 707 g, 77%, b.p. 80°-85° at 0.75 Torr., of colorless distillate which readily crystallized, m.p. 39°-41°.

EXAMPLE 20

Substituted 3-Chloro-1,2-benzisothiazoles (General Method)

The benzisothiazolone was dissolved in dichloroethane (0.04 mole/100 mL) and PCl₅ was added. The mixture was refluxed while monitoring the progress of the reaction by TLC. If the reaction was judged incomplete after one hour at reflux, an additional 0.1–0.5 mole equiv. of PCl₅ was added and refluxed continued until the starting material was consumed. The reaction was cooled, and solvent and excess reagent were removed by distillation under reduced pressure. The residue was flash chromatographed (hexane/methylene chloride) affording the product as a solid.

EXAMPLE 21

3-Chloro-4-methoxy-1,2-benzisothiazole

The 4-methoxy benzisothiazolone (0.065 mole) was dissolved in 200 mL of dichloroethane and PCl₅ (1.05 mole equiv.) was added neat. The reaction was refluxed-monitored by tlc. An additional 0.25 mole equiv. and 2×0.10 mole equiv. of PCl₅ was added after 1 hour, 2½ hours, and 3 hours before the reaction was judged complete by tlc. The reaction was cooled and the solvent and excess reagent removed by house vacuum distillation. The residue was flash chromatographed (30% CH₂Cl₂/70% hexane) affording the 3-chloro-4-methoxy-1,2-benzisothiazole in 60% yield.

Some other examples of substituted 3-chloro-1,2-benzisothiazoles which can be prepared via the general method of Example 20 are shown in Table 3.

TABLE 3

Substituted 3-Chlorobenzisothiazoles

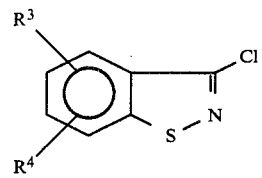

| Ex. | R³ | R⁴ | Yield (%) | m.p. (°C.) |
|-----|------|------|-----------|------------|
| 22 | 4-Cl | 7-MeO | — | — |
| 23 | H | 7-MeO | — | — |
| 24 | H | 6-MeO | 94 | 80–83 |
| 25 | H | 6-Cl | 95 | 99–101 |
| 26 | 4-MeO | H | 98 | — |
| 27 | 5-MeO | H | — | — |
| 28 | 5-OH | H | — | — |
| 29 | 5-MeO | 6-Cl | — | — |
| 30 | 5-MeO | 6-MeO | — | — |

C. Formula III Compounds

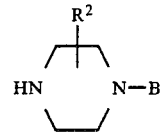

EXAMPLE 31 t-Butyloxycarbonylpiperazine

Benzylpiperazine (0.15 mole) and pulverized K₂CO₃ (0.62 mole equiv.) were combined in 200 mL of 1:1 dioxane/water and mechanically stirred while cooling to 0°. The pyrocarbonate (1.12 mole equiv.) was added, and the reaction was stirred one hour in the cold and then 18 hr at ambient temperature. The dioxane was removed in vacuo and the aqueous phase was extracted (3×methylene chloride), dried (MgSO₄), filtered and concentrated in vacuo to an oil in about 95% crude yield. The oil was divided into two equal portions and each was dissolved in warm absolute ethanol (150 mL), glacial acetic acid (2.1 mole equiv.) and combined with 4.1 g palladium-on-carbon catalyst in a Parr hydrogenation bottle. The mixture was hydrogenated at an initial H₂ pressure of ca. 55 psi until the theoretical amount of hydrogen had been consumed. The mixture was filtered through celite and rinsed with generous amounts of absolute ethanol, then concentrated to the solid product in 84% yield.

Use of this procedure employing benzylpiperazines with appropriate substitution on the piperazine ring will yield the desired t-butyloxycarbonylpiperazines where R² is other than hydrogen.

D. Formula II Compounds

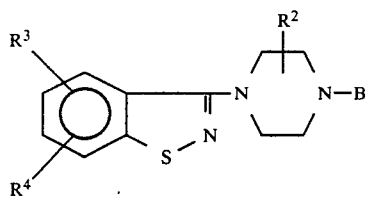

EXAMPLE 32

1-(1,2-Benzisothiazol-3-yl)piperazine

A 4 L suction flask was charged with anhydrous piperazine (1582 g, 18.36 moles) followed by molten 3-chloro-1,2-benzisothiazole (Example 8, 622 g, 3.672 moles). The flask was stoppered with a wired-on rubber stopper and a short length of pressure tubing was wired-on to the side tube. The flask was evacuated (house vacuum) and the pressure tubing on the side arm clamped shut. The apparatus was then oven heated at 125° with occasional swirling as melting proceeded. After 24 hours at this temperature, the orange melt was quenched in 4.8 liter of cracked ice and water. One equivalent of 50% NaOH (293 g, 3.672 moles) was added in one portion. The mixture was extracted with methylene chloride and these extracts washed with water. Concentration in vacuo gave 734 g of crude product which was recrystallized from 1800 mL of boiling ethyl acetate to yield 548 g, 68%, m.p. 88°–90°.

EXAMPLE 33

Substituted 3-(1-Piperazinyl)-1,2-benzisothiazoles

This synthesis proceeds via the 3-(t-butyloxy carbonyl piperazine)-benzisothiazole intermediate with subsequent removal of the t-BOC protective group.

t-Butyloxycarbonylpiperazine (Example 15, 2.5 mole equiv.) was dissolved in anhydrous tetrahydrofuran (0.01–0.02 mole/90 mL) and chilled to −78° under nitrogen with stirring. n-Butyl lithium (2.5 mole equiv.) was added at a rate to keep the temperature less than −70°. The 3-chloro-1,2-benzisothiazole in tetrahydrofuran (1 mole equiv./60 mL) was added dropwise to keep the temperature less than −70°. When the addition was complete, the solution was warmed to 0° and then quenched with 15% aqueous NH$_4$Cl (2.75 mole equiv.). Following concentration in vacuo the residue was extracted with methylene chloride and the extract was washed with 0.5N HCl, dried (MgSO$_4$), filtered and concentrated in vacuo to a semi-solid which was flash chromatographed (hexane/ethyl acetate). These 3-(t-BOC piperazine) benzisothiazole intermediates were generally obtained in 73 to 90% yield.

To remove the t-BOC protective group, the appropriate t-BOC piperazinylbenzisothiazole was taken up in a minimal amount of warm absolute ethanol and acidified with 5N ethanolic HCl (5 mole equiv.), then heated to 90° for ½ hour. Upon cooling, the solvent was removed in vacuo and the crude product recrystallized from absolute ethanol and obtained in yields ranging from 40–60%.

EXAMPLE 34

4-Methoxy-1,2-benzisothiazol-3-yl Piperazine Hydrochloride t-Butyloxycarbonylpiperazine (0.04 mole) was dissolved in 150 mL of anhydrous tetrahydrofuran and chilled to −78° under nitrogen. n-BuLi (0.04 mole) was added at a rate to keep the temperature less than −65°. After 10 minutes, the 4-methoxy-3-chloro-1,2-benzisothiazole (0.016 mole) in 60 mL tetrahydrofuran was added dropwise keeping t<−70°. The reaction was monitored by tlc and judged complete immediately. The ice bath was removed and 15% aqueous NH$_4$Cl (0.044 mole) was added. The mixture was concentrated in vacuo and the residue taken up in CH$_2$Cl$_2$ and washed 1×H$_2$O and 1×cold 0.5N HCl. The methylene chloride was dried on MgSO$_4$, filtered and concentrated in vacuo to the crude product which was flash chromatographed (3:1 hexane/EtOAc) affording the desired material in 73% yield.

The butyloxycarbonylpiperazine benzisothiazole (0.012 mole) was taken up in warm absolute ethanol and acidified with ethanolic HCl (5 mole equiv.). The solution was stirred 30 minutes at 90°. The mixture was cooled and the solvent removed in vacuo. The crude solid was recrystallized from absolute EtOH affording 4-methoxy-1,2-benzisothiazol-3-yl-piperazine hydrochloride in 62% yield.

Examples of additional products which may be obtained using the procedure of Example 33 are shown in Table 4.

TABLE 4

Substituted Formula I 3-(1-piperazinyl)-benzisothiazoles (as HCl salts)

| Ex. | R$^3$ | R$^4$ | Yield (%) | m.p. (°) |
| --- | --- | --- | --- | --- |
| 35 | H | 7-MeO | 40 | 286–290 |
| 36 | 4-Cl | 7-MeO | 37 | 271–274 |
| 37 | H | 6-MeO | 43 | 246–250 |
| 38 | 4-Me | H | 62 | 240–247 |
| 39 | 5-MeO | 6-MeO | | |
| 40 | 5-MeO | 6-Cl | | |
| 41 | 4-CF$_3$ | H | | |

Synthesis of Products

EXAMPLE 42

3-(4-Ethyl-1-piperazinyl)-1,2-benzisothiazole

To 3-(1-piperazinyl)-1,2-benzisothiazole (5.0 g, 0.023 mole) in 25 mL of acetonitrile was added N,N-diisopropylethylamine (3.2 g, 0.025 mole) and bromoethane (2.6 g, 0.024 mole) at 20°. The mixture was refluxed for approximately 3 hr and then concentrated in vacuo; taken up in 5% aqueous K$_2$CO$_3$, and flashed chromatographed with 5% methanol/methylene chloride. The fractions were concentrated in vacuo to yield 4.6 g (0.02 mole, 81%) of an oily product. This product oil was converted to the solid hydrochloride salt by treatment of an ethanol solution with ethanolic HCl. Recrystallization from ethanol gave a white solid, m.p. 230°-232°.

Anal. Calcd. for $C_{13}H_{17}N_3S.HCl.H_2O$: C, 51.90; H, 6.37; N, 13.97. Found: C, 51.65; H, 6.60; N, 14.15.

Using the procedure of Example 22, or an appropriate modification thereof, the individual compounds of Formula I can be readily prepared. Additional examples of these compounds are shown in Table 5.

TABLE 5
Formula I Compounds

| Ex. | $R^1$ | $R^2$ | $R^3$ | $R^4$ | Formula | m.p. (°C.) |
|---|---|---|---|---|---|---|
| 43 | —$CH_3$ | H | H | H | $C_{12}H_{15}N_3S.HCl$ | 250–252 |
| 44 | —$(CH_2)_2CH_3$ | H | H | H | $C_{12}H_{21}N_4S.HCl$ | 222–224 |
| 45 | —$(CH_2)_3CH_3$ | H | H | H | $C_{15}H_{15}N_3S.HCl$ | 209–211 |
| 46 | cyclohexyl | 3-Me | H | H | $C_{17}H_{23}N_3S.HCl$ | 98–100 |
| 47 | —$(CH_2)_4CH_3$ | H | H | H | $C_{16}H_{23}N_3S.HCl$ | 203–204 |
| 48 | —$CH(CH_3)_2$ | H | H | H | $C_{14}H_{19}N_3S.HCl$ | 260–263 |
| 49 | —$(CH_2)_2CH(CH_3)_2$ | H | H | H | $C_{16}H_{23}N_3S.HCl$ | 231–233 |
| 50 | —$CH_2CH=CH_2$ | H | H | H | $C_{14}H_{17}N_3S.HCl$ | 215–217 |
| 51 | —$CH_2$-cyclopropyl | H | H | H | $C_{15}H_{19}N_3S.HCl$ | 243–244 |
| 52 | cyclopentyl | H | H | H | $C_{16}H_{21}N_3S.0.1\ H_2O$ | 134–135 |
| 53 | —$CH_2Ph$ | H | H | H | $C_{18}H_{19}N_3S.HCl$ | 226–228 |
| 54 | —$(CH_2)_3Ph$ | H | H | H | $C_{19}H_{21}N_3S$ | 107–109 |
| 55 | —$(CH_2)_2OPh$ | H | H | H | $C_{19}H_{21}N_3OS$ | 95–95.5 |
| 56 | —$(CH_2)_4OPh$ | H | H | H | $C_{21}H_{25}N_3OS.HCl$ | 181–182 |
| 57 | —$CH_2$-(1,3-benzodioxol-2-yl) | H | H | H | $C_{20}H_{21}N_3O_2S.HCl$ | 206–220 |
| 58 | cyclohexyl | H | H | H | $C_{17}H_{23}N_3S$ | 98–100 |
| 59 | 2-methylcyclohexyl | H | H | H | $C_{18}H_{25}N_3S.HCl$ | 280–290 |
| 60 | indanyl | H | H | H | $C_{20}H_{21}N_3S$ | 139–141 |
| 61 | tetrahydronaphthyl | H | H | H | $C_{21}H_{23}N_3S$ | 114–118 |

TABLE 5-continued

Formula I Compounds

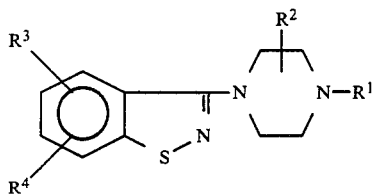

| Ex. | R¹ | R² | R³ | R⁴ | Formula | m.p. (°C.) |
|---|---|---|---|---|---|---|
| 62 | (allyl) | 2-Me | 5-MeO | 6-Cl | | |
| 63 | (cyclopentyl) | | H | H | 6-CF₃ | |

What is claimed is:

1. A compound of Formula I

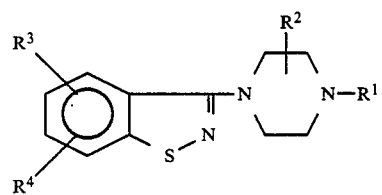

wherein

R¹ is hydrogen, lower ($C_{1-6}$) alkyl, either straight chain or branched, lower alkenyl, lower cycloalkyl, lower cycloalkyl-lower alkylene, phenyl-lower alkylene, phenoxy-lower alkylene, phenyl-lower cycloalkyl, or benzodioxan-2-yl-lower alkylene; with the proviso that R¹ is not hydrogen when R² and R³ are hydrogen and R⁴ is hydrogen or halogen;

R² is lower alkyl or hydrogen; and

R³ and R⁴ are independently chosen from hydrogen, lower alkyl, lower acyloxy, lower alkoxy, lower alkylthio, halogen, hydroxyl, or trifluoromethyl;

or a pharmaceutically acceptable acid addition salt thereof.

2. A compound of claim 1 wherein the lower alkyl, lower alkenyl, lower cycloalkyl, and lower alkylene groups of R¹ contain from 4 to 6 carbon atoms.

3. The compound of claim 1 wherein R¹ is cycloalkyl ($C_{3-6}$).

4. The compound of claim 1, 3-(4-ethyl-1-piperazinyl)-1,2-benzisothiazole.

5. The compound of claim 1, 3-(4-methyl-1-piperazinyl)-1,2-benzisothiazole.

6. The compound of claim 1, 3-(4-propyl-1-piperazinyl)-1,2-benzisothiazole.

7. The compound of claim 1, 3-(4-butyl-1-piperazinyl)-1,2-benzisothiazole.

8. The compound of claim 1, 3-(4-cyclopentyl-3-methyl-1-piperazinyl)-1,2-benzisothiazole.

9. The compound of claim 1, 3-(4-pentyl-1-piperazinyl)-1,2-benzisothiazole.

10. The compound of claim 1, 3-[4-(1-methylethyl)-1-piperazinyl]-1,2-benzisothiazole.

11. The compound of claim 1, 3-[4-(3-methylbutyl)-1-piperazinyl]-1,2-benzisothiazole.

12. The compound of claim 1, 3-[4-(2-propenyl)-1-piperazinyl]-1,2-benzisothiazole.

13. The compound of claim 1, 3-[4-(cyclopropylmethyl)-1-piperazinyl]-1,2-benzisothiazole.

14. The compound of claim 1, 3-(4-cyclopentyl-1-piperazinyl)-1,2-benzisothiazole.

15. The compound of claim 1, 3-[4-benzyl-1-piperazinyl]-1,2-benzisothiazole.

16. The compound of claim 1, 3-[4-(2-phenylethyl)-1-piperazinyl]-1,2-benzisothiazole.

17. The compound of claim 1, 3-[4-(2-phenoxyethyl)-1-piperazinyl]-1,2-benzisothiazole.

18. The compound of claim 1, 3-[4-(4-phenoxybutyl)-1-piperazinyl]-1,2-benzisothiazole.

19. The compound of claim 1, 3-[4-[(1,4-benzodioxan-2-yl)methyl]-1-piperazinyl]-1,2-benzisothiazole.

20. The compound of claim 1, 3-(4-cyclohexyl-1-piperazinyl)-1,2-benzisothiazole.

21. The compound of claim 1, 3-[4-(2-indanyl)-1-piperazinyl]-1,2-benzisothiazole.

22. The compound of claim 1, 3-[4-(1,2,3,4-tetrahydro-2-naphthyl)-1-piperazinyl]-1,2-benzisothiazole.

23. The compound of claim 1, 3-[4-(2-methylcyclohexyl)-1-piperazinyl]-1,2-benzisothiazole.

24. The method for providing an analgesic effect in a mammal in need of analgesia comprising systemic administration to said mammal of an effective analgesic amount of a compound of Formula I wherein R¹ is hydrogen, lower ($C_{1-6}$) alkyl, either straight chain or branched, lower alkenyl, lower cycloalkyl, lower cycloalkyl-lower alkylene, phenyl-lower alkylene, phenoxy-lower alkylene, phenyl-lower cycloalkyl, or benzodioxan-2-yl lower alkylene;

$R^2$ is lower alkyl or hydrogen; and $R^3$ and $R^4$ are independently chosen from hydrogen, lower alkyl, lower acyloxy, lower alkoxy, lower alkylthio, halogen, hydroxyl, or trifluoromethyl;

or a pharmaceutically acceptable acid addition salt thereof.

25. The method of claim 24 wherein the Formula I compound is the compound claimed in claim 3.

26. A pharmaceutical composition in dosage unit form suitable for systemic administration to a mammalian host comprising a pharmaceutical carrier and from about 30 to 600 mg of a compound of Formula I

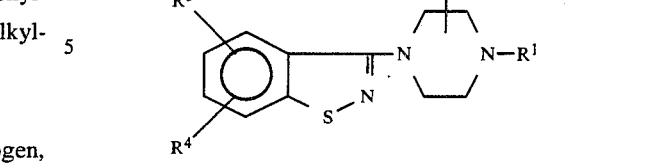

wherein $R^1$ is hydrogen, lower ($C_{1-6}$) alkyl, either straight chain or branched, lower alkenyl, lower cycloalkyl, lower cycloalkyl-lower alkylene, phenyl-lower alkylene, phenoxy-lower alkylene, phenyl-lower cycloalkyl, or benzodioxan-2-yl lower alkylene;

$R^2$ is lower alkyl or hydrogen; and $R^3$ and $R^4$ are independently chosen from hydrogen, lower alkyl, lower acyloxy, lower alkoxy, lower alkylthio, halogen, hydroxyl, or trifluoromethyl;

or a pharmaceutically acceptable acid addition salt thereof.

* * * * *